United States Patent
Löfstedt

(10) Patent No.: US 6,799,073 B2
(45) Date of Patent: Sep. 28, 2004

(54) ELECTRODE TERMINAL FIXING APPLIANCE

(75) Inventor: Charlotte Löfstedt, Kungsängen (SE)

(73) Assignee: St. Jude Medical AB, Järfälla (SE)

( * ) Notice: Subject to any disclaimer, the term of this patent is extended or adjusted under 35 U.S.C. 154(b) by 87 days.

(21) Appl. No.: 10/343,841

(22) PCT Filed: Dec. 13, 2001

(86) PCT No.: PCT/SE01/02781
§ 371 (c)(1),
(2), (4) Date: Feb. 4, 2003

(87) PCT Pub. No.: WO02/49719
PCT Pub. Date: Jun. 27, 2002

(65) Prior Publication Data
US 2004/0015200 A1 Jan. 22, 2004

(30) Foreign Application Priority Data
Dec. 20, 2000 (SE) .............................. 0004764

(51) Int. Cl.$^7$ ............................................. A61N 1/375
(52) U.S. Cl. ...................................................... 607/37
(58) Field of Search .................... 607/37; 439/815–817, 439/811, 908, 810, 431, 723, 729, 793, 822, 578, 835, 860, 909

(56) References Cited

U.S. PATENT DOCUMENTS

| | | | | |
|---|---|---|---|---|
| 1,437,103 A | * | 11/1922 | Hengstenberg | 439/817 |
| 2,907,978 A | * | 10/1959 | Bergan | 439/811 |
| 3,001,173 A | * | 9/1961 | Swengel | 439/822 |
| 3,539,977 A | * | 11/1970 | Woertz | 439/811 |
| 3,836,941 A | * | 9/1974 | Izraeli | 439/431 |
| 4,848,346 A | | 7/1989 | Crawford | |
| 4,860,750 A | | 8/1989 | Frey et al. | |
| 5,076,270 A | | 12/1991 | Stutz, Jr. | |
| 5,086,773 A | | 2/1992 | Ware | |
| 5,964,625 A | * | 10/1999 | Farley | 439/817 |
| 6,112,120 A | | 8/2000 | Correas | |

* cited by examiner

Primary Examiner—George Manuel
(74) Attorney, Agent, or Firm—Schiff Hardin LLP

(57) ABSTRACT

An appliance for fixing the proximal end terminal of an electrode cable into a connector member of an implantable device, such as a heart stimulator, includes a connector insert having a bore for receiving the proximal end of the terminal, and a clamping member for fixing the terminal in the bore by clamping. The clamping member is axially movable in a shaft opening in the insert, which proceeds through and across the bore. The clamping member is an unthreaded pin which is held in said shaft opening, but which is axially movable therein, and is biased in the shaft opening by a spring toward a position wherein an inner end of the pin is able to engage a side of the terminal exposed in the shaft opening. The inner end of the pin has a diametrically extending recess, which is alignable with the terminal during insertion thereof into the bore. The inner end of the shaft further has two diametrically aligned depressions disposed at a right angle to the recess, the pin being able to fix the terminal by clamping action after rotating the pin for aligning the depressions with the terminal in the bore.

8 Claims, 2 Drawing Sheets

ELECTRODE TERMINAL FIXING APPLIANCE

BACKGROUND OF THE INVENTION

1. Field of the Invention

The present invention relates to an appliance for fixing the proximal end terminal of an electrode cable to a connector member of an implantable medical device, e.g. a heart stimulator, such as a pacemaker or a defibrillator. More particularly, the appliance of the present invention is of the type having a connector insert having a hole for receiving the terminal, and a member for clamping the terminal to fix it in the insert, the clamping member being axially movable in a shaft in the insert which adjoins and crosses said hole, wherein the clamping member has the shape of an unthreaded pin which is held in the shaft so as to be movable axially within limits in the shaft and biased by a spring toward a position therein such that an inner end of the pin is capable of engaging a side of the terminal being exposed in the shaft, the inner end of the pin having a diametrically extending recess to be aligned with the terminal during insertion thereof into the hole.

2. Description of the Prior Art

In a most general and simple type of lead appliance, fixing, the proximal terminal of the electrode cable is axially fixed in the connector member by means of a set screw, which is screwed into a transverse threaded shaft in order to radially press the electrode terminal against contact surfaces of the connector member to thereby achieve fixing of the terminal by clamping. The use of screws requires accurate assembly instructions and a precise tightening torque to be applied to the screw.

Various kinds of screwless electrode fixing devices have been developed. For example, U.S. Pat. No. 4,860,750 discloses a wedge element for fixing a lead in an asymmetrical manner which does not ensure a constant clamping force within the tolerance range of the lead. Also, achievement of safe body fluid sealing of the wedge element requires careful efforts.

U.S. Pat. No. 4,848,346 discloses two circular springs which could be expanded to allow insertion of a heart lead by depressing a straight end portion of the springs protruding from the outer surface of the connector block. However, such protruding end portions may cause unintentional release of the heart lead.

U.S. Pat. No. 6,112,120 discloses an apparatus for connecting a bipolar proximal end terminal of an electrode cable to a connector member of an implantable medical device. The apparatus has two connection outputs, each having a spring-biased electrical contact element exerting a radial pressure on a respective terminal portion. The terminal is fixed in the medical device by means of a separate locking wedge.

SUMMARY OF THE INVENTION

An object of the present invention is to provide an improved electrode terminal fixing appliance having an unthreaded fixation pin which is capable of safely snap-lock the terminal in the connector insert only by turning the pin a quarter of a revolution. This object is achieved in an appliance of the type initially described wherein the inner end of the pin has two diametrically aligned depressions at a right angle to the recess, the depressions having a smaller depth than the recess so that the pin is capable of fixing the terminal by clamping action after rotating the pin for aligning the depressions with the terminal.

DESCRIPTION OF PREFERRED EMBODIMENTS

Figure 1:
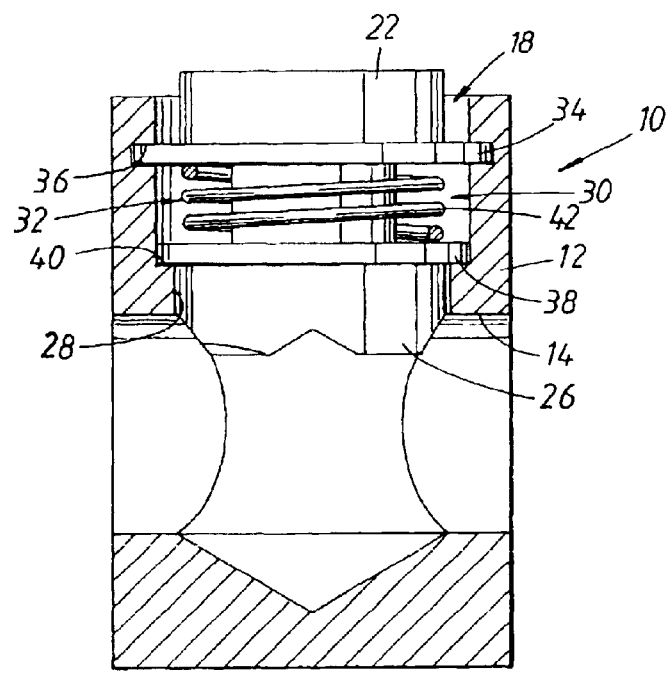
FIG. 1 is an enlarged side view of an electrode terminal fixing appliance of the present invention in an inactive position, in which it is ready for receiving a proximal end terminal of a heart stimulator electrode to be fixed in a connector member of the stimulator.
Figure 2:
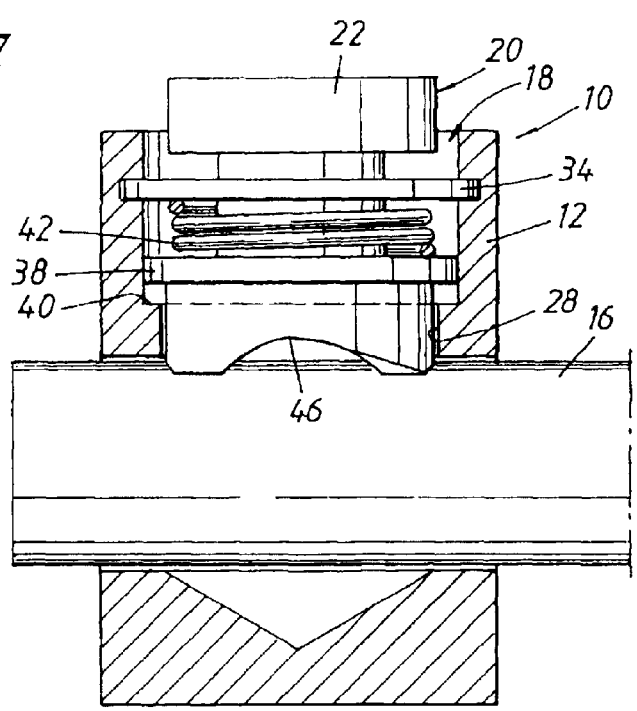
FIG. 2 is a side view similar to FIG. 1 but showing the appliance in an active position in which a spring-biased captive fixing pin has been rotated 90° and is securely holding a proximal end terminal having been inserted into a through-hole in a connector insert piece.

FIG. 1 shows an electrode terminal fixing appliance 10 of the present invention intended for use in an implantable medical device (not shown), in particular a pacemaker or defibrillator. The appliance 10 is adapted to be mounted in a connector member of the medical device which connects an electronic unit of the device with a proximal end terminal of an electrode cable which is adapted to be inserted through veins and to be anchored at a distal end thereof in the heart. The fixing appliance 10 has a connector insert block 12 having a bore or through-hole 14 for receiving the proximal end terminal 16 (FIG. 2) of the electrode cable (not shown). A stepped blind hole or shaft 18 extending transversely to the through-hole 14 houses an unthreaded clamping pin 20 in a captive manner such that it can move axially within certain limits and rotate 90° between a terminal receiving position (FIG. 1) and a terminal fixating position (FIG. 2). The pin 20 has a first cylindrical part 22 which is guided in a wider section 24 of the stepped shaft 18, and a second cylindrical part 26 that is guided in a narrow section 28 of the shaft 18. Between the two cylindrical parts 22, 26 of the pin there is a recess 30 for holding a spring unit 32 for biasing the pin 20 towards a first axial position (FIG. 1). The spring unit 32 has a first washer 34, which is axially secured in a circular groove 36 in the wider section of the shaft 18, and a second washer 38 which is biased against a shoulder 40 of the recess 30 by a helical compression spring element 42. In the first axial position of the pin 20, as shown in FIG. 1, the second washer 38 rests against a step 44 between the wider and narrow sections of the shaft 18. A concave recess 46 (FIGS. 2 and 3) having a perimeter or profile corresponding to the cross-section of the proximal end terminal 16 is formed at the inner end of the pin 20 and is aligned with the through-hole 14 in the position shown in FIG. 1 so as to allow for unobstructed insertion of the terminal 16 into the insert block 12.

Figure 3:
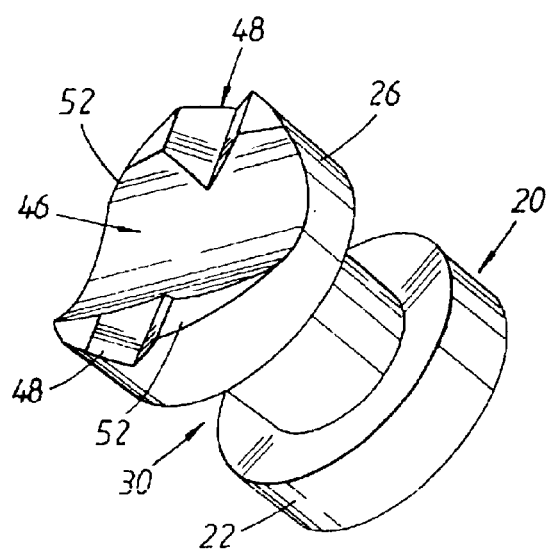
FIG. 3 is a further enlarged perspective view of the fixing pin.

As shown in FIGS. 1 and 3, two diagonally opposed, notch-like depressions 48 are formed transversely to the concave recess 46 at the end of the pin 20 and are adapted to form pressure seats which engage and fixate the proximal terminal 16 in the connector block 12 in a second axial position of the pin 20, as shown in FIG. 2. In order to make it possible to bring the pin 20 from its first axial, terminal receiving position in FIG. 1 to its second axial, terminal fixing position in FIG. 2, the pin 20 has to be rotated 90° by a tool, such as a screw driver, key wrench or the like, engaging with a corresponding slot or the like (not shown) in the outer end 50 of the pin 20. To facilitate the rotation of the pin 20 there are formed diagonally opposed, inclined circumferential cam surfaces 52 at the inner end of the pin 20, so that the pin 20 is smoothly lifted against the action of the compression spring element 42 during the rotation of the pin and the notch-like depressions 48 snap-fits into engagement with the periphery of the terminal 16. The spring element 42 has an appropriate stiffness to cause the pin 20 to exert a sufficient clamping pressure on the terminal 16 to safely lock the same in the connector block 12.

It is conceivable to form the washers 34, 38 as integral end parts of the spring element 42 in order to minimize the number of components.

Figure 4:
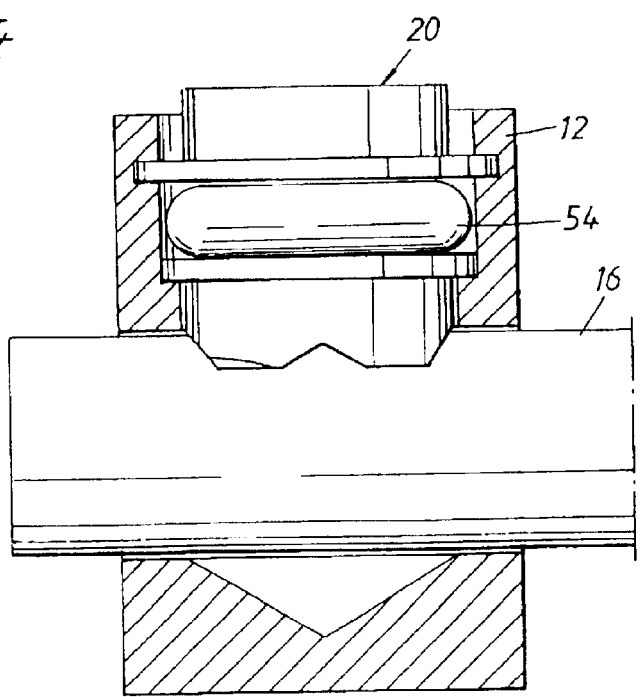
FIG. 4 is a side view of a second embodiment of the appliance of the present invention, using an elastic O-ring as a combined spring-biasing and sealing means.

According to a second embodiment of the fixing appliance of the present invention shown in FIG. 4, the spring unit biasing the pin 20 towards a clamping position on the terminal 16 may be formed as a stiff O-ring 54 which also acts as a sealing ring preventing body fluids from reaching the respective contact surfaces between the terminal 16 and the connector block 12.

Although modifications and changes may be suggested by those skilled in the art, it is the invention of the inventor to embody within the patent warranted heron all changes and modifications as reasonably and property come within the scope of her contribution to the art.

What is claimed is:

1. An appliance for fixing a proximal end terminal of an electrode to an implantable device, said appliance comprising:

a connector member forming a portion of an implantable device, said connector member having a connector insert with a bore therein adapted to receive a proximal end terminal of an electrode, said insert further having a shaft opening proceeding through said bore;

a clamping member an axially movable within said shaft opening adapted to interact with a terminal in said bore for fixing said terminal in said bore by clamping, said clamping member being an unthreaded pin constrained for said axial movement within said shaft opening and biased in said shaft opening by a spring toward a position wherein an inner end of said pin engages a side of said terminal exposed in said shaft, said inner end of said pin having a recess extending diametrically across said pin and alignable with said terminal during insertion of said terminal into said bore; and said inner end of said pin further having two diametrically aligned depressions disposed at a right angle to said recess, said depressions having a depth which is smaller than said recess causing fixing of said terminal in said bore by said pin by clamping action upon rotation of said pin to align said depressions with said terminal.

2. An appliance as claimed in claim 1 wherein said inner end of said pin has two diagonally opposed, circumferentially extending inclined ramp surfaces allowing rotation of said pin through a quarter of a revolution to displace said pin, against said spring, away from an inner position to a clamping position in which said terminal is supported by said two diametrically aligned depressions.

3. An appliance as claimed in claim 2 wherein said pin has a delimiting element for limiting rotation of said pin.

4. An appliance as claimed in claim 1 wherein said spring is a helical compression spring acting between axially facing surfaces of respective recesses in said shaft opening and in said pin.

5. An appliance as claimed in claim 4 further comprising respective washers disposed between said compression springs and said axially facing surfaces.

6. An appliance as claimed in claim 1 wherein said spring comprises an annular elastic member disposed between axially facing surfaces of respective recesses in said shaft and in said pin.

7. An appliance as claimed in claim 6 wherein said annular member is an O-ring.

8. An appliance as claimed in claim 1 further comprising a screwdriver slot aligned with said bore, disposed at an outer end of said pin.

* * * * *